(12) United States Patent
Shigemori et al.

(10) Patent No.: US 8,184,148 B2
(45) Date of Patent: May 22, 2012

(54) RECEIVING APPARATUS

(75) Inventors: Toshiaki Shigemori, Hachioji (JP); Manabu Fujita, Hino (JP); Ayako Nagase, Hachioji (JP); Akira Matsui, Hino (JP); Kazutaka Nakatsuchi, Hino (JP)

(73) Assignee: Olympus Corporation (JP)

( * ) Notice: Subject to any disclaimer, the term of this patent is extended or adjusted under 35 U.S.C. 154(b) by 1119 days.

(21) Appl. No.: 11/577,446

(22) PCT Filed: Aug. 29, 2006

(86) PCT No.: PCT/JP2006/017004
§ 371 (c)(1),
(2), (4) Date: Apr. 18, 2007

(87) PCT Pub. No.: WO2007/026711
PCT Pub. Date: Mar. 8, 2007

(65) Prior Publication Data
US 2009/0046821 A1    Feb. 19, 2009

(30) Foreign Application Priority Data

Aug. 29, 2005    (JP) ................. 2005-250106

(51) Int. Cl.
*H04N 7/18*    (2006.01)

(52) U.S. Cl. ........................................................ 348/77

(58) Field of Classification Search ..................... 348/77
See application file for complete search history.

(56) References Cited

U.S. PATENT DOCUMENTS 7,596,359 B2    9/2009    Kimoto et al.
2001/0051766 A1*    12/2001    Gazdzinski ................... 600/309
2002/0173718 A1    11/2002    Frisch et al. ................... 600/424
2003/0085994 A1*    5/2003    Fujita et al. ..................... 348/77
2004/0138558 A1*    7/2004    Dunki-Jacobs et al. ....... 600/431
2004/0242962 A1    12/2004    Uchiyama ...................... 600/118
2006/0158512 A1*    7/2006    Iddan et al. ..................... 348/68
2006/0209185 A1*    9/2006    Yokoi .............................. 348/65
2007/0058036 A1*    3/2007    Shigemori et al. .............. 348/77
2010/0249508 A1*    9/2010    Sato et al. ....................... 600/117

FOREIGN PATENT DOCUMENTS

JP    2002-085333    3/2002
JP    2003-19111    1/2003
JP    2004-200736    7/2004

(Continued)

OTHER PUBLICATIONS

Japanese Office Action dated Feb. 7, 2011 in corresponding Japanese Patent Application No. 2005-25106.
PCT International Search Report dated Nov. 14, 2006 issued in corresponding PCT Application No. PCT/JP2006/317004.
Chinese Office Action dated Dec. 18, 2009 in corresponding Chinese Patent Application No. 2006-80031659.7.

(Continued)

*Primary Examiner* — Ajay Bhatia
(74) *Attorney, Agent, or Firm* — Ostrolenk Faber LLP (57) ABSTRACT

A capsule endoscope 3 is inserted into a subject and transmits a capsule ID, which is received by an RF receiving unit 11 of a receiving apparatus 2. A capsule ID detecting circuit 19 detects the capsule ID. A control unit C recognizes a type of the capsule endoscope 3 based on the detected capsule ID, and changes over a threshold of received field strength of a receiving antenna. Thus, a content of processing for the capsule endoscope 3 is changed over, and a selection controller C1 selects a receiving antenna for an image receiving period from receiving antennas A1 to An.

18 Claims, 6 Drawing Sheets

FOREIGN PATENT DOCUMENTS

| JP | 2004-328941 | 11/2004 |
| --- | --- | --- |
| JP | 2004-350963 | 12/2004 |
| JP | 2005-143991 | 6/2005 |
| JP | 2005-192819 | 7/2005 |

OTHER PUBLICATIONS

Australian Office Action dated Apr. 1, 2009 in corresponding Australian Patent Application No. 2006285872.

* cited by examiner

RECEIVING APPARATUS

CROSS REFERENCE TO RELATED APPLICATION

The present application is a 35 U.S.C. §§371 national phase conversion of PCT/JP2006/317004, filed Aug. 29, 2006, which claims priority of Japanese Application No. 2005-250106, filed Aug. 30, 2005. The PCT International Application was published in the Japanese language.

TECHNICAL FIELD

The present invention relates to a receiving apparatus which performs predetermined processing on information transmitted from a body insertable device such as a capsule endoscope which is introduced into a subject and acquires intra-subject information.

BACKGROUND ART

In recent years, a capsule endoscope having an imaging function and a radio communication function appears in a field of endoscope. After being swallowed by a patient, i.e., a subject (human body), from the mouth for an observation (examination), the capsule endoscope travels through inside internal organs (body cavities) such as esophagus, stomach, and small intestine following peristaltic movements and sequentially captures images using the imaging function until naturally discharged from a living body of the subject, in other word, during an observation period.

During the observation period in which the capsule endoscope travels through the internal organs, the capsule endoscope captures images in the body cavities thereby obtaining image data, and sequentially transmits the image data to an outside of the subject using the radio communication function, i.e., by radio communication. Then, the image data is accumulated in a memory inside a receiving apparatus provided outside the subject. When the subject carries the receiving apparatus equipped with the radio communication function and the memory function, the subject can move freely without inconveniences even after swallowing the capsule endoscope and before discharging the same, i.e., even during the observation period. After the observation finishes, a doctor can display images inside the body cavities on a display unit or the like based on the image data accumulated in the memory of the receiving apparatus, and make diagnosis (see Patent Document 1, for example).

There are various types of capsules corresponding to areas whose images are to be captured, for example, there are capsules for esophagus, stomach, small intestine, and the like. The capsule starts imaging after reaching a relevant organ. Further, some capsules that travel through body cavities following the peristaltic motions measure pH, temperature, and the like in the body cavity, and transmit measurement data to the receiving apparatus outside.

Patent Document 1: Japanese Patent Application Laid-Open No. 2003-19111

DISCLOSURE OF INVENTION

Problem to be Solved by the Invention

Patent Document 1, however, does not describe how the receiving apparatus recognizes each capsule and what kind of processing the receiving apparatus performs, and therefore it appears to be difficult to use one receiving apparatus for various types of capsules.

In view of the foregoing, an object of the present invention is to provide a receiving apparatus which can recognize a type of a body insertable device and change over a content of processing according to the type of the body insertable device.

Means for Solving Problem

To solve the problems as described above and to achieve an object, a receiving apparatus according to one aspect of the present invention includes a receiver which receives information transmitted from a body insertable device; a recognizing unit which recognizes supplied identification information of the body insertable device; a process switcher which gives an instruction to change over a content of processing based on a result of recognition by the recognizing unit; and a processor which performs predetermined processing based on the instruction from the process switcher.

The receiving apparatus according to the invention, may further include a detector which detects the identification information of the body insertable device received by the receiver, and the recognizing unit may recognize the identification information based on a supplied result of detection by the detector.

The receiving apparatus according to the invention, may further include an input unit which accepts an input of the identification information of the body insertable device from an outside, and the recognizing unit may recognize the identification information based on the input from the input unit.

The receiving apparatus according to the invention, may further include a taking-in unit, provided on the apparatus, which takes in the identification information of the body insertable device, and the recognizing unit may recognize the identification information supplied from the taking-in unit.

In the receiving apparatus according to the invention, the identification information transmitted from the body insertable device may have a header which indicates a type of the body insertable device.

In the receiving apparatus according to the invention, the instruction supplied by the process switcher may include at least one of an instruction to change over a threshold of received field strength of an antenna provided in the receiver, an instruction to change over a frame rate for display, an instruction to change over image processing for image processing, an instruction by control signals to control the body insertable device.

Effect of the Invention

The receiving apparatus according to the present invention includes the recognizing unit which recognizes the supplied identification information of the body insertable device, and the switching unit which gives an instruction to change over the content of processing, whereby the receiving apparatus can change over the content of processing to be performed and perform suitable processing for each capsule endoscope.

EXPLANATIONS OF LETTERS OR NUMERALS

1 Subject
2 Receiving apparatus
2a Receiving jacket
2b External device
2c Transmitting/receiving jacket
3 Capsule endoscope
4 Display device
5 Communication cable
11 RF receiving unit
12 Signal processing circuit
13 Storage unit
14 Display unit
15 Sample-and-hold circuit
16 A/D converter
17 Power supply unit
18 Interface unit
19 Capsule ID detecting circuit
20 Clock generation circuit
21 Command input unit
22 RF transmitting unit
A1 to An Receiving antenna
B Transmitting antenna
C Control unit
C1 Selection controller
CON, CONb Connecting unit
CON1 to CONn, CONm Connector
SC Switching controller
SW Changeover switch

BEST MODE(S) FOR CARRYING OUT THE INVENTION

Exemplary embodiments of a receiving apparatus according to the present invention will be described in detail below with reference to the accompanying drawings of FIGS. 1 to 6. It should be noted that the present invention is not limited to the embodiments and various modifications can be made without departing from the scope of the present invention.

First Embodiment

Figure 1:
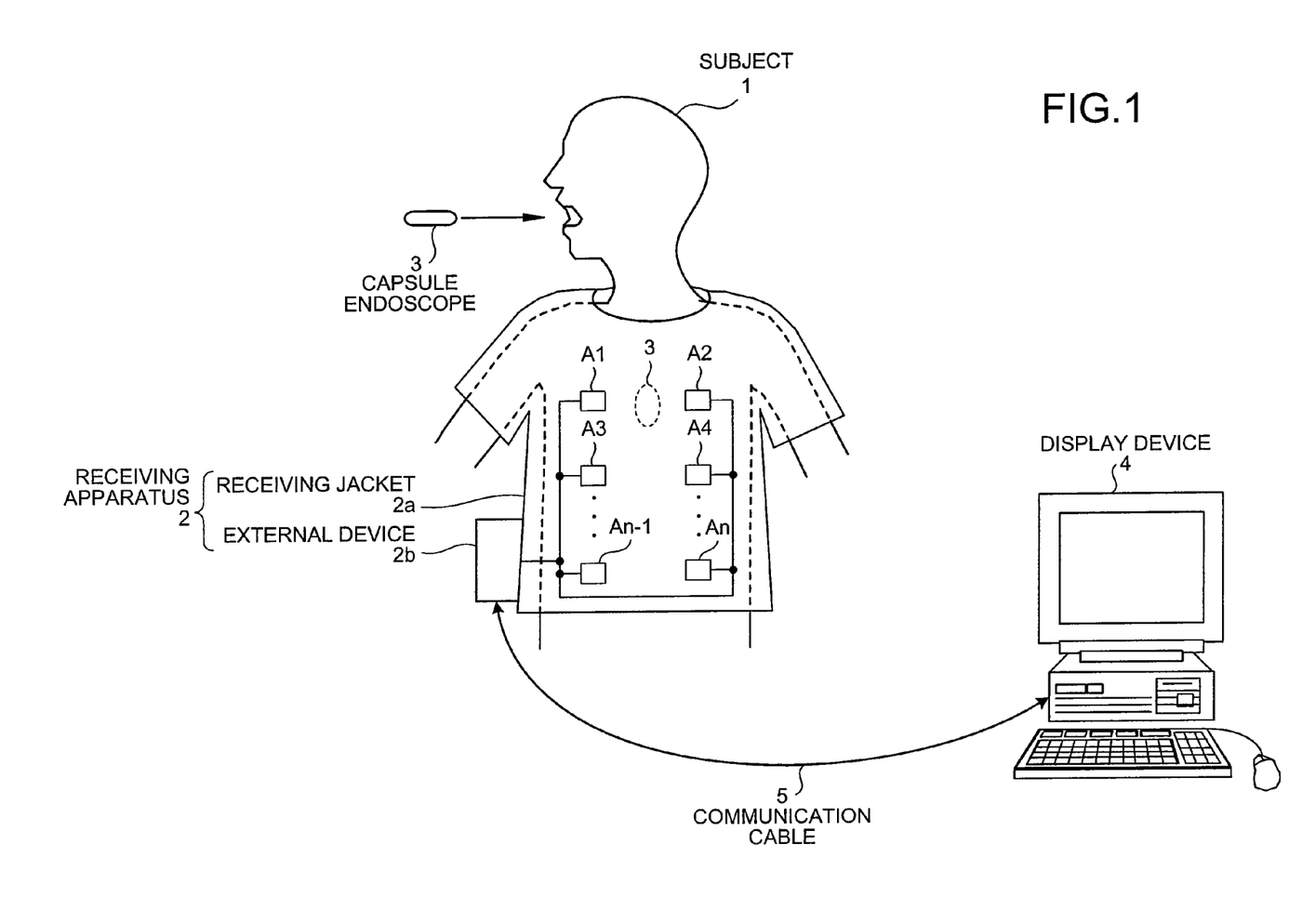
FIG. 1 is a schematic diagram of an overall structure of a wireless in-vivo information acquiring system provided with a medical apparatus according to the present invention.

FIG. 1 is a schematic diagram of an overall structure of a wireless in-vivo information acquiring system provided with a medical apparatus according to the present invention. The wireless in-vivo information acquiring system includes a capsule endoscope as an example of a body insertable device, and the receiving apparatus according to the present invention is configured so as to change over a content of processing according to a type of the capsule endoscope. In the first embodiment, a capsule endoscope 3 has a transmitting antenna for transmitting image information and the like, and the transmitting antenna has a different arrangement and directional characteristic according to the type of the capsule endoscope 3. A description will be given on how the receiving apparatus receives a capsule ID, which indicates the type of the capsule endoscope 3 and is transmitted from the capsule endoscope 3 by radio, and changes over the content of processing.

In FIG. 1, the wireless in-vivo information acquiring system includes a receiving apparatus 2 which has a radio reception function, and the capsule endoscope 3 which is introduced into a subject 1, captures images inside body cavities, and transmits data such as image signals to the receiving apparatus 2. Further, the wireless in-vivo information acquiring system includes a display device 4 which displays images inside the body cavities based on the image signals received by the receiving apparatus 2, and a communication cable 5 which serves for data transfer between the receiving apparatus 2 and the display device 4. The receiving apparatus 2 includes a receiving jacket 2a which is worn by the subject 1, and an external device 2b which performs, for example, processing on received radio signals.

The display device 4 serves to display images obtained by the capsule endoscope 3 inside the body cavities, and has a structure like a workstation that displays images based on data obtained from the receiving apparatus 2 via the communication cable 5. Specifically, the display device 4 may directly display images as in a Cathode Ray Tube (CRT) display and a liquid crystal display. Alternatively, the display device 4 may output images onto other media as in a printer.

Generally, the communication cable 5 can be attached to and detached from the external device 2b and the display device 4, and data information can be retrieved from or recorded into the external device 2b while the communication cable 5 is attached to the external device 2b and the display device 4. In the first embodiment, the communication cable 5 is connected between the external device 2b and the display device 4 so that data can be transmitted from the display device 4 to the external device 2b at initialization of the receiving apparatus 2. The receiving apparatus 2 is initialized, for example, when previous data such as image data stored in a storage unit 13 during a previous examination is to be deleted, or when identification information of a patient and an examination ID including a date of examination are to be registered. After the initialization is finished, the communication cable 5 is disconnected from the external device 2b and the display device 4 to cut the connection between the external device 2b and the display device 4. While the capsule endoscope 3 travels through the body cavities of the subject 1, the connection between the external device 2b and the display device 4 remains cut. The external device 2b receives and records data transmitted from the capsule endoscope by radio. After the capsule endoscope 3 is discharged from the subject 1, in other words, after the imaging inside the subject 1 is finished, the communication cable 5 is connected between the external device 2b and the display device 4, and the display device 4 reads out the data transmitted from the capsule endoscope 3 and recorded in the external device 2b. The communication between the external device 2b and the display device 4 according to the present invention can be realized not only by the communication cable 5 but by radio.

Figure 2:
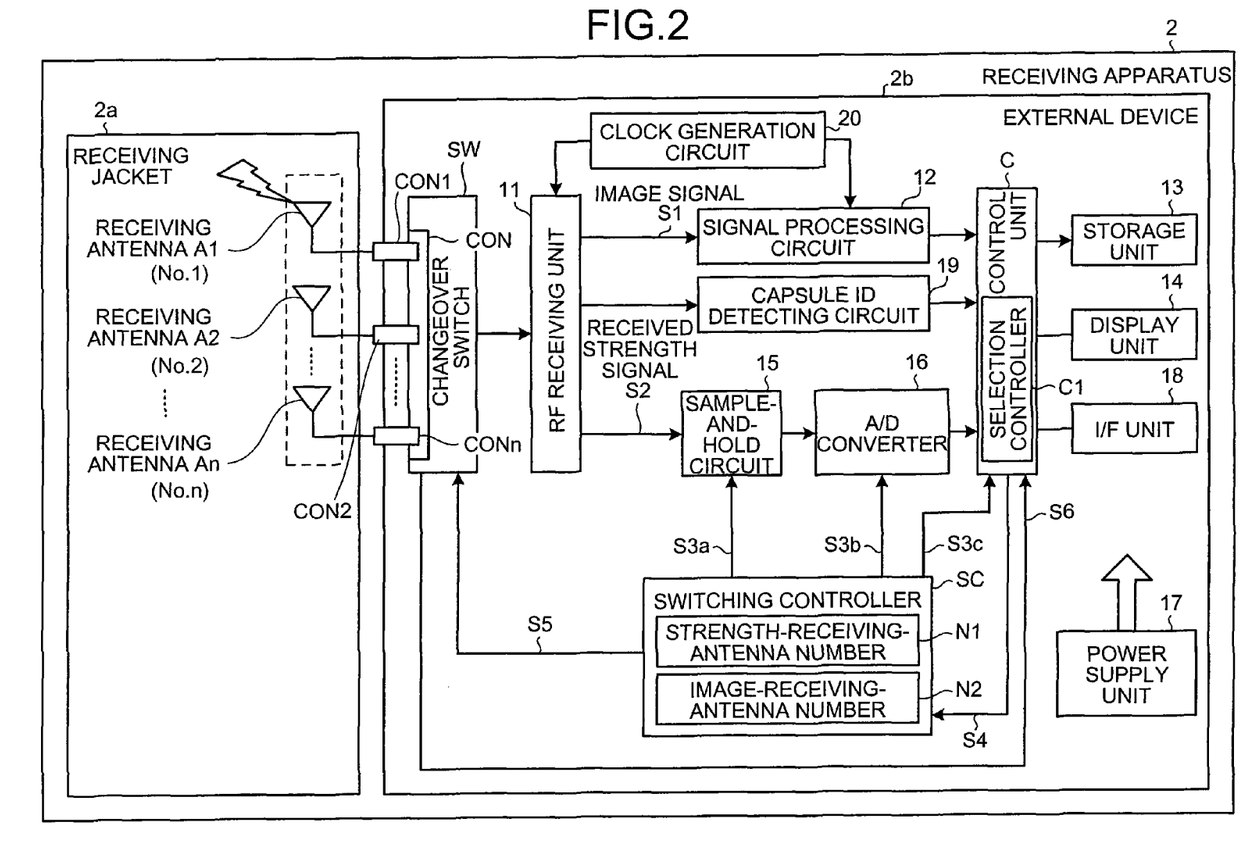
FIG. 2 is a block diagram of a first embodiment of a structure of a receiving apparatus shown in FIG. 1.

A structure of the receiving apparatus according to the first embodiment will be described with reference to the block diagram of FIG. 2. The receiving apparatus 2 has a function of receiving image data of an interior of the body cavities when the image data is transmitted from the capsule endoscope 3 by radio. As shown in FIG. 2, the receiving apparatus 2 is formed so as to be worn by the subject 1, and includes the receiving jacket 2a provided with receiving antennas A1 to An, and the external device 2b which performs, for example, processing of radio signals received by the receiving jacket 2a. The receiving antennas A1 to An may be directly attached onto an outer surface of the subject (human body) 1, rather than being attached to the receiving jacket 2a. The receiving antennas A1 to An may be detachable from the receiving jacket 2a.

The external device 2b has a function of processing the radio signals transmitted from the capsule endoscope 3. Specifically, the external device 2b, as shown in FIG. 2, includes a changeover switch SW which changes over a connection to each of the receiving antennas A1 to An, and an RF receiving unit 11 (receiver) which is connected in a subsequent stage of the changeover switch SW to amplify and demodulate the radio signals transmitted from the receiving antenna connected via the change-over by the changeover switch SW among the receiving antennas A1 to An. Further in a subsequent stage of the RF receiving unit 11, a signal processing circuit 12, a sample-and-hold circuit 15, and a capsule ID detecting circuit 19 (detector) are connected. In a subsequent stage of the sample-and-hold circuit 15, an A/D converter 16 is connected. Between the RF receiving unit 11 and the signal processing circuit 12, a clock generation circuit 20 is connected to synchronize timing of operations.

Figure 3:
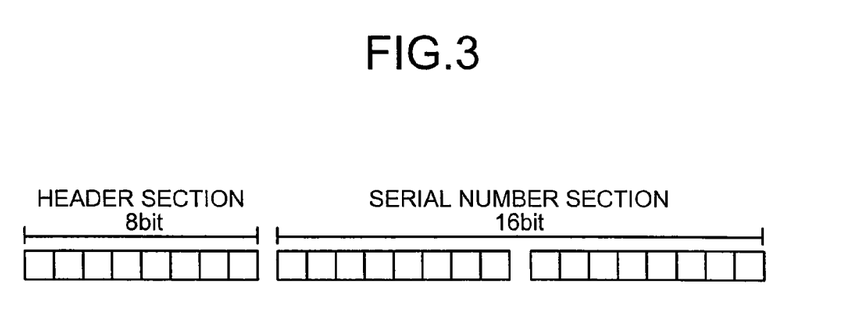
FIG. 3 shows an example of a format of a capsule ID.

The capsule ID detecting circuit 19 detects a capsule ID which is identification information of the capsule endoscope 3 and appended to the signals transmitted from the capsule endoscope 3. FIG. 3 shows an example of a format of the capsule ID. The capsule ID consists of, as shown in FIG. 3, an 8-bit header section and a 16-bit serial number section, for example. The header section is employed to distinguish a type of the capsule endoscope, and up to 256 types of capsule endoscopes can be distinguished based on the header section. The serial number section indicates a number of the capsule endoscopes, and is able to indicate up to 65,536 capsule endoscopes.

A control unit C (process switcher, processor) includes a selection controller C1 (processor) which works as a controller. The control unit C connects the signal processing circuit 12, the A/D converter 16, the storage unit 13 which includes a hard disk or the like to store the image data, a display unit 14, an interface unit 18, and a switching controller SC. The switching controller SC stores a strength-receiving-antenna number N1 and an image-receiving-antenna number N2. The switching controller SC gives a switching instruction to the changeover switch SW based on information on the numbers mentioned above, and gives instructions on processing timing of the sample-and-hold circuit 15, the A/D converter 16, and the selection controller C1. The interface unit 18 is connected to the communication cable 5 via a connecting unit not shown. The control unit C has an internal memory not shown, and registers identification information in the internal memory. The identification information includes an examination ID or the like which identifies the subject, and is supplied through the interface unit 18 and the communication cable 5. A power supply unit 17 includes, for example, a commercially available battery, and supplies power to the internal devices mentioned above.

The changeover switch SW of the external device 2b supplies the radio signals received by the receiving antennas A1 to An to the RF receiving unit 11 based on a switching instruction from the switching controller SC. The changeover switch SW has a connecting unit CON corresponding to the arranged positions of the receiving antennas A1 to An, and the connecting unit CON serves as an antenna switcher to connect to each of the receiving antennas A1 to An.

The connecting unit CON has a function of detecting a connection state of each of connectors CON1 to CONn. Specifically, the connecting unit CON has a detecting unit to detect an antenna-disconnected state of the connector CON1 and is configured to output a voltage signal as a detection signal to the selection controller C1 when the connector CON1 is connected to the connecting unit CON. The connecting unit CON has a similar detecting unit to detect the antenna-disconnected state for each of the other connectors CON2 to CONn. Thus, the selection controller C1 can determine whether the connector CON1, hence the receiving antenna A1, is connected or not by detecting whether the voltage signal is supplied or not. Since the connecting unit CON has the similar detecting units corresponding respectively to the connectors CON2 to CONn, the selection controller C1 can determine whether each of the receiving antennas A1 to An is connected or not.

In FIG. 2, the RF receiving unit 11 amplifies and demodulates the radio signals, as described above, and outputs the resulting image signals S1 to the signal processing circuit 12. At the same time, the RF receiving unit 11 outputs received strength signals S2, which indicates strength of a received electric field of the amplified radio signals, to the sample-and-hold circuit 15. The image data is processed by the signal processing circuit 12, and the processed image data is stored in the storage unit 13 and displayed by the display unit 14 under the control of the control unit C. The sample-and-hold circuit 15 samples and holds the signals, and the A/D converter 16 converts the resulting signals into digital signals, which are taken into the control unit C. The control unit C selects the receiving antenna which receives a highest electric-field strength as the receiving antenna for an image signal period and also sequentially selects each of the remaining antennas as the receiving antenna for a strength-receiving period. The control unit C sends signals S4, in which the each receiving antenna is numbered either by the image-receiving-antenna number N2 or the strength-receiving-antenna number N1, to the switching controller SC. The selection controller C1 sets only the receiving antennas which are actually connected among the receiving antennas A1 to An as a target of switching based on signals S6.

In the first embodiment, the capsule endoscope 3 may have a different arrangement and directional characteristic of the transmitting antenna which transmits the image information and the like according to the type of the capsule endoscope 3, as described above. Therefore, the control unit C is required to change a threshold of the received field strength for the receiving antennas A1 to An to accommodate such difference. Therefore, the control unit C stores capsule ID information of each capsule endoscope in association with threshold information of the received field strength of the receiving antenna in an internal memory not shown. The control unit C reads out the relevant threshold information of the received field strength according to the capsule ID detected by the capsule ID detecting circuit 19, and changes over the content of processing (threshold of the received field strength), thereby selecting the receiving antenna which receives the highest electric-field strength as the receiving antenna for the image signal period.

Further, the control unit C stores the received field strength of the strength receiving period and the received field strength of the image receiving period each in association with the selected receiving antenna in the storage unit 13 together with the image data. The stored received field strength of each receiving antenna is utilized for calculating the position of the capsule endoscope 3 in the body cavity at the reception of image data.

The switching controller SC stores the strength-receiving-antenna number N1 and the image-receiving-antenna number N2 as indicated by the selection controller C1, and supplies signals S5 to the changeover switch SW so as to give commands to the changeover switch SW to selectively connect the receiving antenna A1 to An which corresponds to the strength-receiving-antenna number N1 during the strength receiving period and to selectively connect the receiving antenna A1 to An which corresponds to the image-receiving-antenna number N2 during the image receiving period. At the same time, the switching controller SC supplies signals S3$a$ to designate sample-and-hold timing to the sample-and-hold circuit 15, supplies signals S3$b$ to designate A/D conversion timing to the A/D converter 16, and supplies signals S3$c$ to designate selection control timing to the selection controller C1.

Thus, in the first embodiment, the receiving apparatus side detects the capsule ID transmitted from the capsule endoscope, changes over the threshold of the received electric-field strength (content of processing) of the receiving antenna based on the detected capsule ID, and selects the receiving antenna for the image receiving period, whereby the receiving apparatus can change over the content of processing for the body insertable device by recognizing the type of the body insertable device. Thus, the suitable processing can be performed for each capsule endoscope.

In the first embodiment, the capsule ID is transmitted from the capsule endoscope 3. The present invention, however, is not limited thereto. For example, the capsule ID may be transmitted at the initialization from the display device 4 (workstation) provided outside and connected via the interface unit 18 which serves as an input unit. Further, the receiving apparatus 2 may be provided with a front panel or a barcode reader as a unit to take in the capsule ID. Then, the capsule ID may be taken in through a touch input on the front panel, or barcode information corresponding to each capsule ID may be read by the barcode reader so that the capsule ID is taken in.

Second Embodiment

The capsule endoscopes 3 may be classified into different types based on an area whose image is to be captured, for example, there are capsule endoscopes for small intestine, esophagus, and stomach. Among these types of capsule endoscopes 3, a capsule endoscope for small intestine captures images of the subject at an imaging rate of 2 fps (2 frames per second); has a battery whose life is eight hours (in other words, time required until the examination ends is eight hours); and has a monocular configuration provided with a single imaging element arranged in a travel direction of the capsule endoscope 3 for image capturing. A capsule endoscope for esophagus captures images of the subject at an imaging rate of 15 fps (15 frames per second); has a battery whose life is one hour (in other words, time required until the examination ends is one hour); has a compound-eye configuration provided with plural imaging elements arranged in a radial direction perpendicular to the travel direction of the capsule endoscope 3; and requires image processing in the receiving apparatus 2 for real-time observation. A capsule endoscope for stomach captures images of the subject at an imaging rate of 8 fps (8 frames per second); has a battery whose life is two hours (in other words, time required until the examination ends is two hours); has the compound-eye configuration provided with plural imaging elements arranged in the radial direction perpendicular to the travel direction of the capsule endoscope 3; and requires image processing in the receiving apparatus 2 for the real-time observation.

Figure 4:
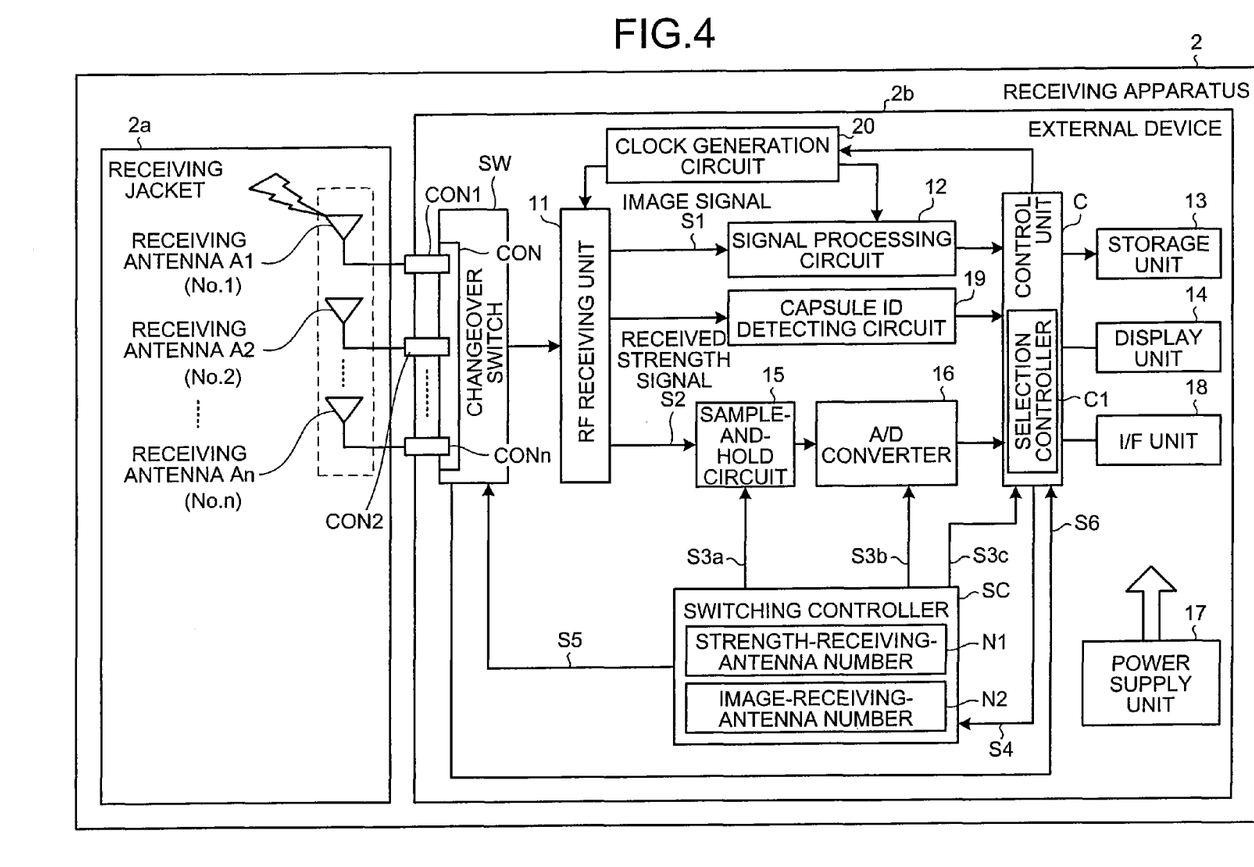
FIG. 4 is a block diagram of a second embodiment of the structure of the receiving apparatus shown in FIG. 1.

A structure of the receiving apparatus 2 which can be employed with various types of capsule endoscopes as described above is shown in FIG. 4. FIG. 4 is a block diagram of a second embodiment of the structure of the receiving apparatus shown in FIG. 1. As shown in FIG. 4, the receiving apparatus 2 of the second embodiment is different from the receiving apparatus 2 of the first embodiment in that the clock generation circuit 20 (processor) can generate clocks at different frequencies, and that the control unit C (process switcher) controls the clock generation circuit 20 so as to change the frequency of the generated clock.

Since the capsule endoscope 3 may have different imaging rate depending on the region to be examined, such as small intestine, esophagus, and stomach, the control unit C serves to change a frame rate for image display, for example, in accordance with the imaging rate, and makes a relevant unit operate accordingly. Specifically, the control unit C changes the frame rate by supplying a command to the clock generation circuit 20 according to the capsule ID, and thereby changing the frequency of the clock supplied to the RF receiving unit 11 and the signal processing circuit 12 to an optimal level.

Thus, in the second embodiment, the receiving apparatus side detects the capsule ID transmitted from the capsule endoscope, changes the frame rate of the receiving apparatus based on the detected capsule ID, and switches to an optimal operation timing, whereby the receiving apparatus of the second embodiment can recognize the type of the body insertable device and change over the content of processing for the body insertable device similarly to the first embodiment. Therefore, the receiving apparatus of the second embodiment can perform suitable processing for each capsule endoscope.

Third Embodiment

When the receiving apparatus 2 is employed with the capsule endoscope 3 dedicated for a particular examined region as in the second embodiment, the receiving apparatus 2 may be required to perform image processing for the real-time observation (display) in the receiving apparatus 2, as mentioned above.

Figure 5:
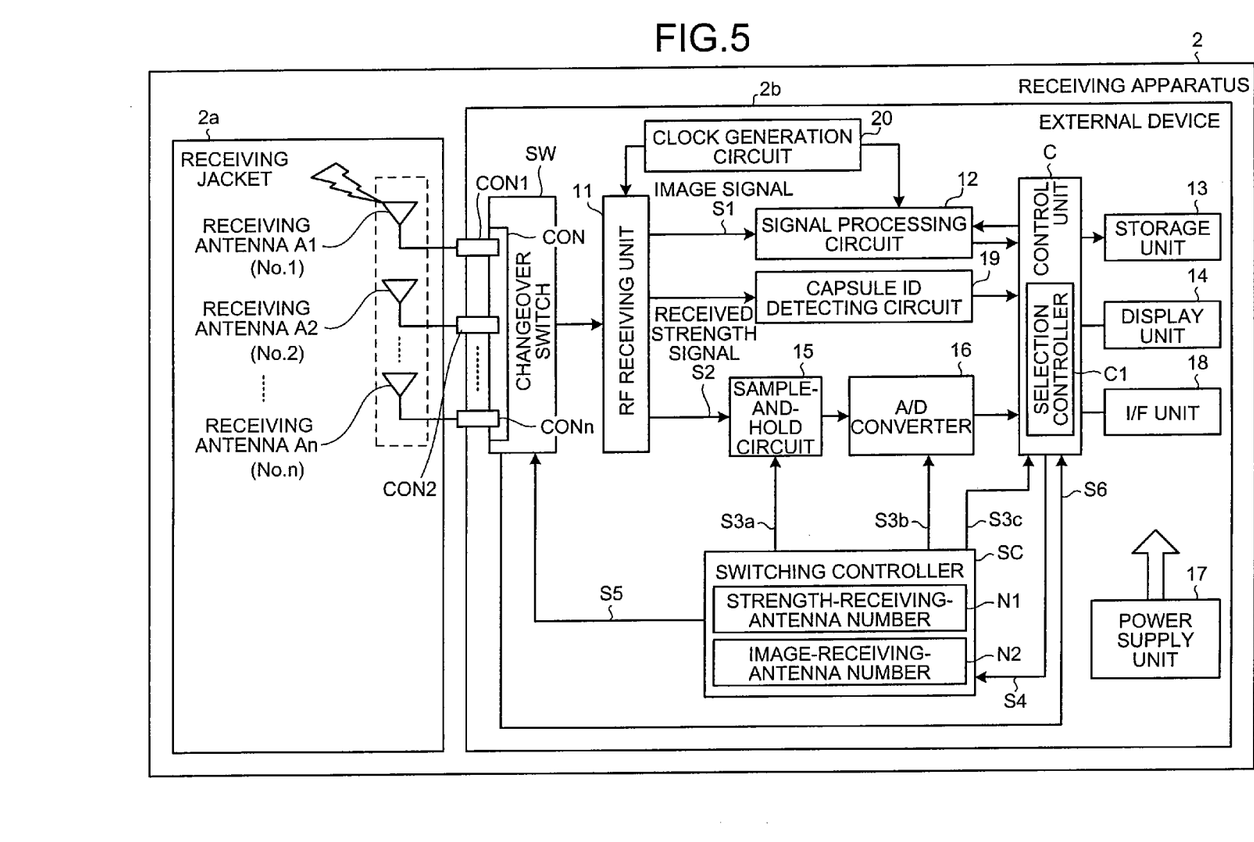
FIG. 5 is a block diagram of a third embodiment of the structure of the receiving apparatus shown in FIG. 1.

Shown in FIG. 5 is the receiving apparatus 2 which meets the requirement as described above. FIG. 5 is a block diagram of a third embodiment of the structure of the receiving apparatus shown in FIG. 1. As can be seen from FIG. 4, the receiving apparatus 2 of the third embodiment is different from the receiving apparatus 2 of the first embodiment in that the control unit C (process switcher) changes over the content of processing by supplying coefficients to be employed by the signal processing circuit 12 (processor) for processing, e.g., enhancement such as luminance correction and color processing such as gamma correction (hereinafter such processing will be referred to as "image processing") to the signal processing circuit 12 as a command.

In the third embodiment, the receiving apparatus side detects the capsule ID transmitted from the capsule endoscope and changes over the content of image processing in the receiving apparatus based on the detected capsule ID. Therefore, similarly to the first and the second embodiments, the receiving apparatus can recognize the type of the body insertable device and change over the content of image processing according to the type of the body insertable device. Thus, the receiving apparatus of the third embodiment can perform suitable processing for each capsule endoscope.

Other than the image processing as described above, the receiving apparatus may perform processing such as selection of the size of the image according to the capsule ID. When the image size is to be selected, an image size selection circuit may be provided between the RF receiving unit 11 and the signal processing circuit 12. The control unit C may supply a command to change over the image size to the image size selection circuit and the signal processing circuit 12, whereby the size of the image to be processed at the receiving apparatus may be changed.

Fourth Embodiment

Further, the body insertable devices may be classified into different types based on the function and purpose of use, for example, there are a capsule for pH detection which detects pH level in the examined region, a capsule for temperature detection which detects temperature at the examined region, a DDS capsule which is used in a drug delivery system (DDS) to administer drug at the examined region, an externally-driven capsule which introduces power from outside, and a self-propelled capsule which controls rotation thereof according to changes in an external magnetic field.

Among the above mentioned capsules, the pH detection capsule and the temperature detection capsule require processing of the detected data on pH and temperature; the DDS capsule requires timing control for drug administration; the externally-driven capsule requires power supply from outside, and the self-propelled capsule requires application of the external magnetic field and rotation correction of captured images.

Figure 6:
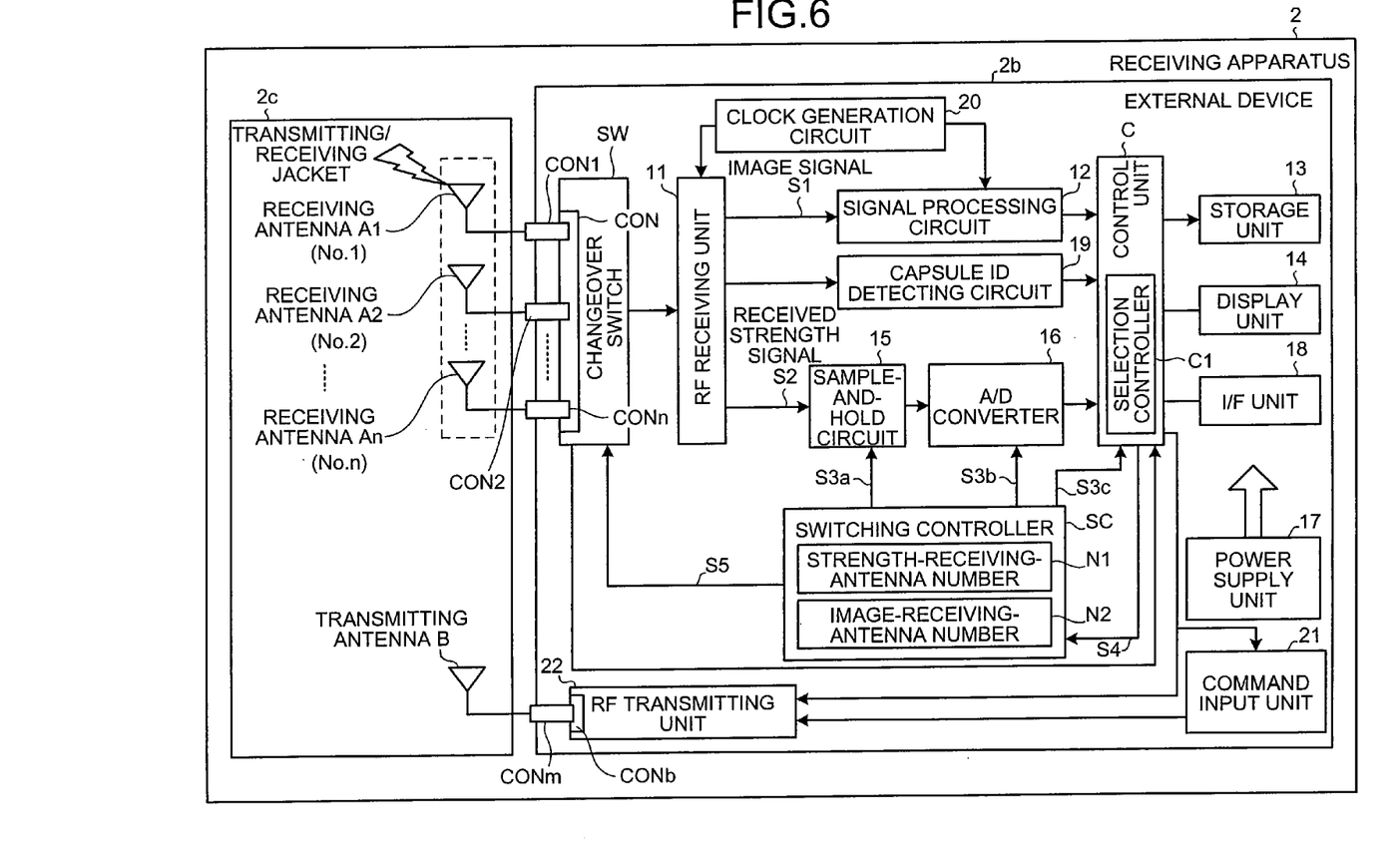
FIG. 6 is a block diagram of a fourth embodiment of the structure of the receiving apparatus shown in FIG. 1.

Shown in FIG. 6 is the receiving apparatus 2 which can be applied to the above mentioned types of capsules. FIG. 6 is a block diagram of a fourth embodiment of the structure of the receiving apparatus shown in FIG. 1. As shown in FIG. 6, the receiving apparatus 2 of the fourth embodiment is different from the receiving apparatus 2 of the first embodiment in that the receiving apparatus 2 of the fourth embodiment includes a command input unit 21 (processor) which serves to supply a command to an RF transmitting unit 22 according to a switching instruction from the control unit C (process switcher), and the RF transmitting unit 22 (processor) which converts the command supplied from the command input unit 21 to RF signals and radio transmits the obtained RF signals via a transmitting antenna B. The transmitting antenna B is arranged on a transmitting/receiving jacket 2*c*, which is shaped so as to be worn by the subject 1, together with the receiving antennas A1 to An. The RF transmitting unit 22 has a connector CONb which is electrically connected with a connector CONm of the transmitting antenna B.

The command input unit 21 supplies commands such as a command for processing the data on pH or temperature, a command for timing control, a command for performing processing so as not to receive signals during power supply from outside, and a command for rotation correction of the captured images.

In the fourth embodiment, a bidirectional communication between the receiving apparatus 2 and the capsule endoscope 3 is made possible under the control of the control unit C so that the receiving apparatus 2 can transmit a pertinent command corresponding to the received capsule ID sent from the capsule endoscope 3 to the capsule endoscope 3. The control unit C also controls ON and OFF of the RF transmitting unit 22.

As can be seen from the above, in the fourth embodiment, the receiving apparatus side detects the capsule ID transmitted from the capsule endoscope, and selectively transmits a command for controlling the capsule endoscope based on the detected capsule ID. Therefore, the receiving apparatus of the fourth embodiment can recognize the type of the body insertable device and change over the content of processing for the body insertable device similarly to the first to the third embodiments. Thus, the receiving apparatus can perform suitable processing for each capsule endoscope.

Further, the receiving apparatus of the present invention can indirectly control the power consumption of the power supply unit 17 by controlling the RF receiving unit 11 and/or the RF transmitting unit 22 according to the capsule ID so that the RF receiving unit 11 and/or the RF transmitting unit 22 operate intermittently, or by controlling an access speed of a memory (not shown) inside the signal processing circuit 12.

INDUSTRIAL APPLICABILITY

As can be seen from the foregoing, the receiving apparatus according to the present invention is useful for a medical observation apparatus which is introduced into a human body for an observation of an examined region, and in particular suitable for a receiving apparatus which recognizes the type of the body insertable device to allow for a changeover of the content of processing for the body insertable device.

The invention claimed is:

1. A receiving apparatus comprising:
a receiver which receives information transmitted from a body insertable device;
a recognizing unit which recognizes supplied identification information of the body insertable device;
a process switcher which gives an instruction to change over a content of processing based on a result of recognition by the recognizing unit; and
a processor which performs predetermined processing based on the instruction from the process switcher, wherein
the instruction supplied by the process switcher includes at least one of an instruction to changed over a threshold of received field strength of an antenna provided in the receiver, an instruction to change over a frame rate for display, an instruction to change over image processing for image processing, an instruction by control signals to control the body insertable device, an instruction to control change-over of an image size, and an instruction to control an intermittent operation.

2. The receiving apparatus according to claim 1, further comprising
a detector which detects the identification information of the body insertable device as received by the receiver, wherein the recognizing unit recognizes the identification information based on a supplied result of detection by the detector.

3. The receiving apparatus according to claim 1, further comprising
an input unit which accepts an input of the identification information of the body insertable device from an outside, wherein the recognizing unit recognizes the identification information based on the input from the input unit.

4. The receiving apparatus according to claim 1 further comprising
a taking-in unit which takes in the identification information of the body insertable device, wherein the recognizing unit recognizes the identification information supplied from the taking-in unit.

5. The receiving apparatus according to claim 1, wherein the identification information transmitted from the body insertable device includes a header information section which indicates a type of the body insertable device.

6. The receiving apparatus according to claim 1, wherein the instruction to change over the frame rate for display causes frequency of a clock generated by a clock generation circuit in the receiving apparatus to be changed.

7. The receiving apparatus according to claim 1, wherein the instruction to change over image processing for image processing causes plural types of image processing to be identified according to an identification number.

8. The receiving apparatus according to claim 7, wherein the instruction to change over image processing for image processing causes units performing image processing including luminance correction and color correction to be identified according to the identification number.

9. The receiving apparatus according to claim 1, wherein the instruction to control the intermittent operation causes one of a transmission process and a reception process of the radio signal to be controlled so that one of the transmission process and the reception process is performed intermittently.

10. The receiving apparatus according to claim 1, wherein the instruction to control the intermittent operation causes an access speed of a memory to be controlled.

11. The receiving apparatus according to claim 5, wherein the identification information includes a serial number section which is specific to the body insertable device.

12. The receiving apparatus according to claim 4, wherein the taking-in unit receives the identification information from a display device which displays an image captured by the body insertable device.

13. The receiving apparatus according to claim 4, wherein the taking-in unit receives the identification information through a touch panel provided on the receiving apparatus.

14. The receiving apparatus according to claim 4, wherein the taking-in unit receives the identification information as information consisting of a black and white stripe pattern.

15. A reception method comprising:
receiving information transmitted from a body insertable device;
recognizing supplied identification information of the body insertable device;
supplying an instruction to change over a content of processing based on a result of recognition in the recognizing; and
performing predetermined processing based on the instruction supplied, wherein
the instruction supplied in the supplying includes at least one of an instruction to change over a threshold of received field strength of an antenna, an instruction to change over a frame rate for display, an instruction to change over image processing for image processing, an instruction by control signals to control the body insertable device, an instruction to control chan e-over of an image size, and an instruction to control an intermittent operation.

16. The reception method according to claim 15, further comprising detecting the identification information of the body insertable device as received in the receiving, wherein the identification information is recognized based on a result of the detecting.

17. The reception method according to claim 15, further comprising accepting an input of the identification information of the body insertable device from an outside, wherein the identification information is recognized in the recognizing based on the input accepted.

18. The reception method according to claim 15, further comprising taking in the identification information of the body insertable device, wherein the identification information taken-in is recognized in the recognizing.

* * * * *